(12) United States Patent
Wu et al.

(10) Patent No.: US 7,758,625 B2
(45) Date of Patent: Jul. 20, 2010

(54) DELIVERY SYSTEM FOR MEDICAL DEVICES

(75) Inventors: Patrick P. Wu, Mountain View, CA (US); Keif Fitzgerald, San Jose, CA (US); August Yambao, Temecula, CA (US); Michael Green, Pleasanton, CA (US)

(73) Assignee: Abbott Vascular Solutions Inc., Santa Clara, CA (US)

( * ) Notice: Subject to any disclaimer, the term of this patent is extended or adjusted under 35 U.S.C. 154(b) by 1941 days.

(21) Appl. No.: 10/661,406

(22) Filed: Sep. 12, 2003

(65) Prior Publication Data
US 2005/0060016 A1   Mar. 17, 2005

(51) Int. Cl.
*A61F 2/06* (2006.01)

(52) U.S. Cl. .................................... 623/1.11

(58) Field of Classification Search ............... 623/1.11, 623/1.12, 902, 903; 606/108, 200, 192–198, 606/205–209, 86 A, 86 R, 99; 254/97; 600/585, 600/184; 604/523, 528, 103.04, 158, 164.07, 604/164.08, 165.01, 165.02, 171, 174, 239; 403/353; 285/114–116, 401, 402
See application file for complete search history.

(56) References Cited

U.S. PATENT DOCUMENTS

| | | | |
|---|---|---|---|
| 4,624,243 A * | 11/1986 | Lowery et al. | 600/136 |
| 4,665,918 A | 5/1987 | Garza et al. | |
| 5,346,498 A | 9/1994 | Greelis et al. | |
| 5,501,654 A * | 3/1996 | Failla et al. | 600/204 |
| 5,507,768 A | 4/1996 | Lau et al. | |
| 5,571,168 A | 11/1996 | Del Toro | |
| 5,683,451 A | 11/1997 | Lenker et al. | |
| 5,707,376 A * | 1/1998 | Kavteladze et al. | 623/1.11 |
| 5,733,267 A | 3/1998 | Del Toro | |
| 5,833,694 A | 11/1998 | Poncet | |
| 5,868,755 A | 2/1999 | Kanner et al. | |
| 5,906,619 A * | 5/1999 | Olson et al. | 606/108 |
| 5,920,975 A | 7/1999 | Morales | |
| 5,944,727 A | 8/1999 | Ahari et al. | |
| 6,146,415 A * | 11/2000 | Fitz | 623/1.11 |
| 6,165,184 A * | 12/2000 | Verdura et al. | 606/148 |
| 6,183,443 B1 * | 2/2001 | Kratoska et al. | 604/164.03 |

(Continued)

FOREIGN PATENT DOCUMENTS

EP      0747021 A    12/1996

(Continued)

*Primary Examiner*—Todd E Manahan
*Assistant Examiner*—Elizabeth Houston
(74) *Attorney, Agent, or Firm*—Fulwider Patton LLP; Jonathan Feuchtwang

(57) ABSTRACT

A delivery system for implantation a self-expanding medical device in a body includes a control handle and a catheter portion. The catheter portion includes an outer restraining member which covers the collapsed, medical device, an inner catheter member having a distal end including a region upon which the medical device is mounted, and an outer sheath removably attached to the control handle. The outer sheath creates a conduit for the catheter portion to prevent the inner catheter member from moving axially when the outer restraining member is retracted. The control handle has a rotatable thumbwheel to actuate a retraction mechanism attached to the proximal end of the outer restraining member which moves the restraining member in a proximal direction to deploy the medical device.

18 Claims, 5 Drawing Sheets

U.S. PATENT DOCUMENTS

| | | |
|---|---|---|
| 6,190,360 B1 | 2/2001 | Iancea et al. |
| 6,203,550 B1 | 3/2001 | Olson |
| 6,254,611 B1 | 7/2001 | Vrba |
| 6,258,101 B1 * | 7/2001 | Blake, III .................. 606/113 |
| 6,391,050 B1 | 5/2002 | Broome |
| 6,391,051 B2 | 5/2002 | Sullivan, III et al. |
| 6,514,261 B1 | 2/2003 | Randall et al. |
| 6,527,779 B1 | 3/2003 | Rourke |
| 6,669,716 B1 * | 12/2003 | Gilson et al. .............. 623/1.11 |
| 6,755,854 B2 * | 6/2004 | Gillick et al. ............. 623/1.11 |
| 6,866,669 B2 * | 3/2005 | Buzzard et al. ............. 606/108 |
| 7,122,050 B2 | 10/2006 | Randall et al. |

FOREIGN PATENT DOCUMENTS

| | | | |
|---|---|---|---|
| WO | WO 99/49808 | * | 10/1999 |
| WO | 2002087470 A | | 11/2002 |

* cited by examiner

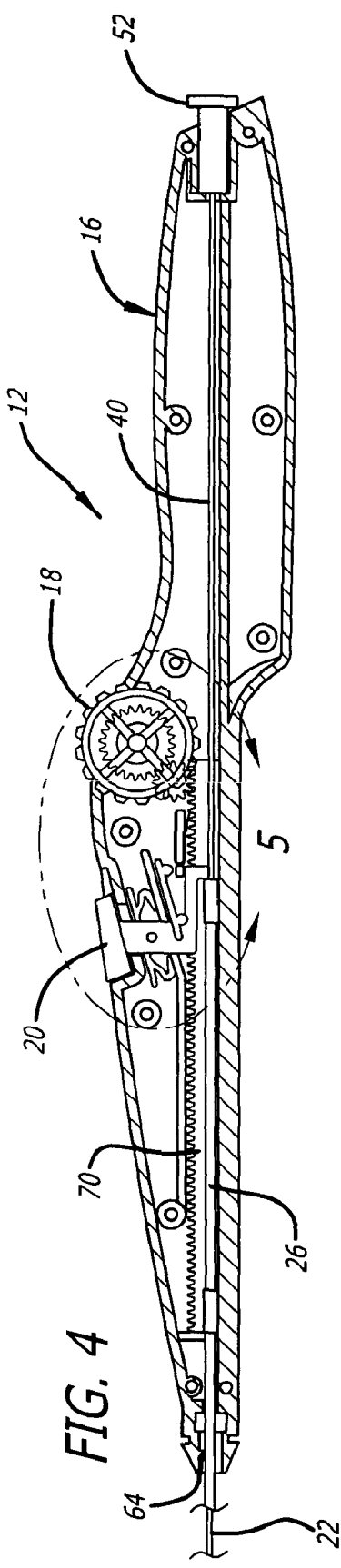
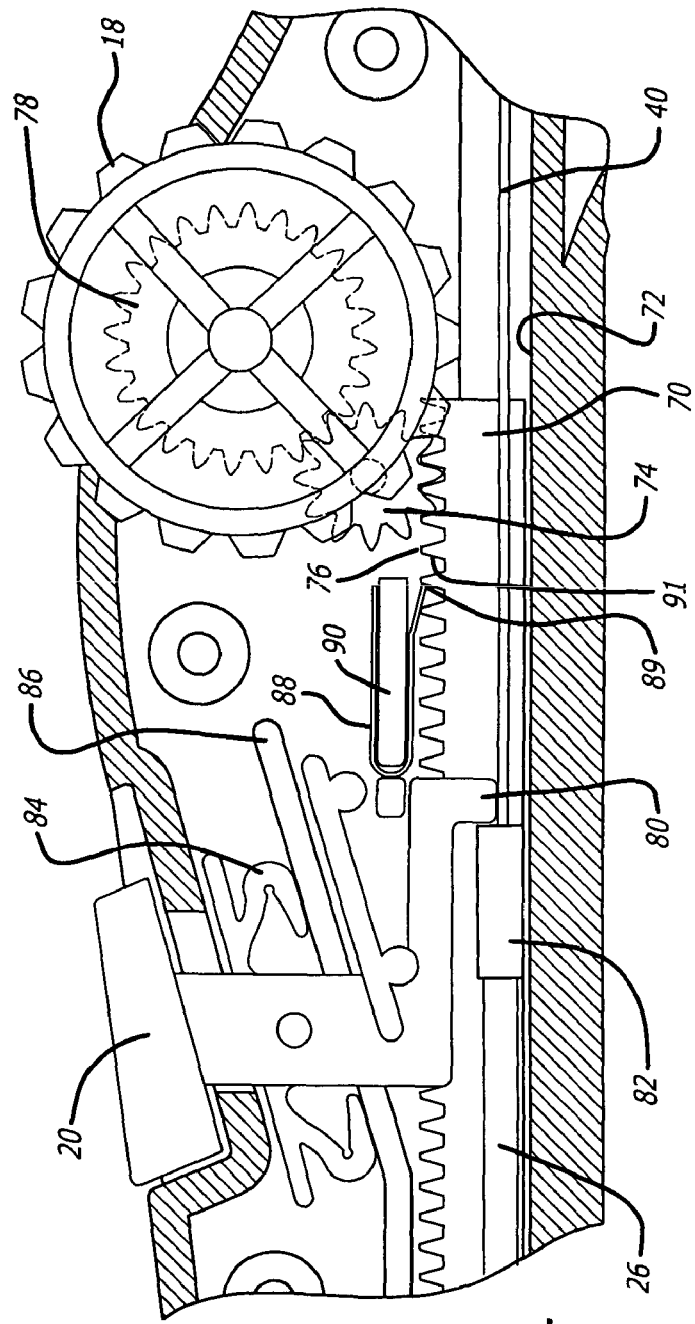
FIG. 4
FIG. 5

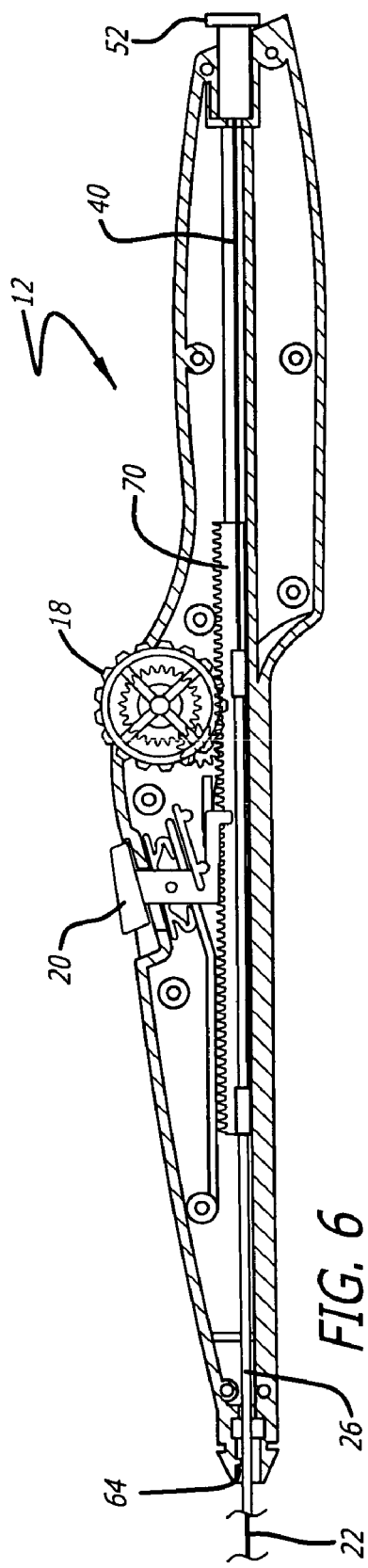
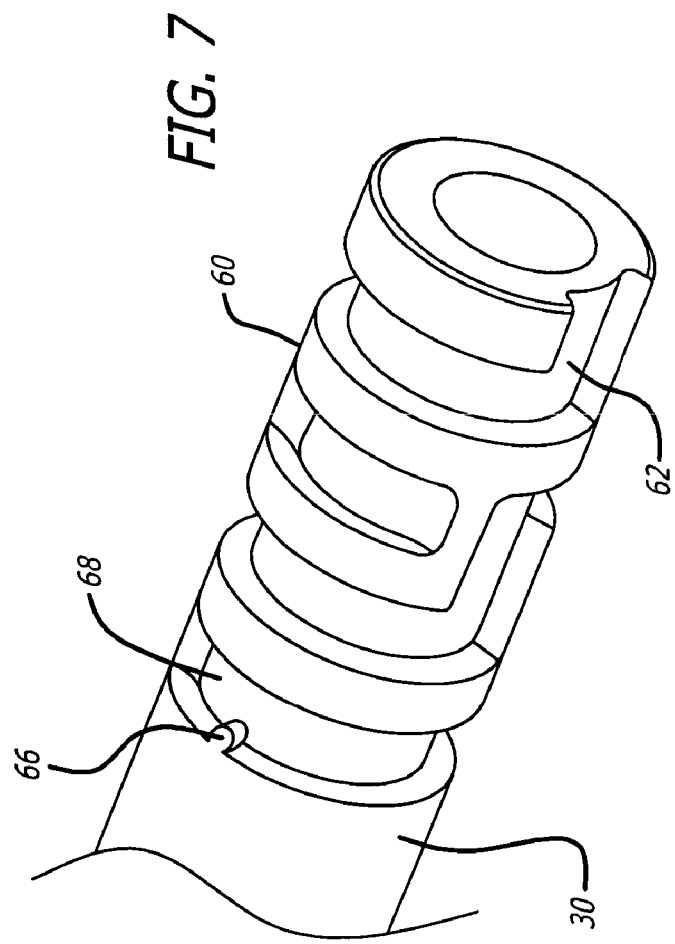

DELIVERY SYSTEM FOR MEDICAL DEVICES

BACKGROUND OF THE INVENTION

The present invention relates generally to delivery systems for delivering and deploying medical devices, such as stents, which are adapted to be implanted into a patient's body, such as a blood vessel and, more particularly, to a delivery system for more accurately deploying a self-expanding medical device into an area of treatment.

Stents are generally cylindrically shaped devices which function to hold open and sometimes expand a segment of a blood vessel or other arterial lumen, such as coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis. Stents, or stent-like devices, are often used as the support and mounting structure for implantable vascular grafts which can be used to create an artificial conduit to bypass the diseased portion of the vasculature, such as an abdominal aortic aneurism.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery and accommodate the often tortuous path of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from shape memory metals or super-elastic nickel-titanium (NiTi) alloys, which will automatically expand from a compressed state when the stent is advanced out of the distal end of the delivery, or when a restraining sheath which holds the compressed stent in its delivery position is retracted to expose the stent.

Some prior art stent delivery systems for delivery and implanting self-expanding stents include an member lumen upon which the compressed or collapsed stent is mounted and an outer restraining sheath which is initially placed over the compressed stent prior to deployment. When the stent is to be deployed in the body vessel, the outer sheath is moved in relation to the inner member to "uncover" the compressed stent, allowing the stent to move to its expanded condition. Some delivery systems utilize a "push-pull" type technique in which the outer sheath is retracted while the inner member is pushed forward. Another common delivery system utilizes a simple pull-back delivery system in which the self-expanding stent is maintained in its compressed position by an outer sheath. Once the mounted stent has been moved at the desired treatment location, the outer sheath is pulled back via a deployment handle located at a remote position outside of the patient, which uncovers the stent to allow it to self-expand within the patient. Still other delivery systems use an actuating wire attached to the outer sheath. When the actuating wire is pulled to retract the outer sheath and deploy the stent, the inner member must remain stationary, preventing the stent from moving axially within the body vessel.

However, problems have been associated with such prior art delivery systems. For example, systems which rely on a "push-pull design" or "push-back design" can experience unwanted movement of the collapsed stent within the body vessel when the inner member is pushed forward which can lead to inaccurate stent positioning. Systems which utilize a "pull back" system or an actuating wire design will tend to move to follow the radius of curvature when placed in curved anatomy of the patient. As the outer sheath member is actuated, tension in the delivery system can cause the system to straighten. As the system straightens, the position of the stent changes because the length of the catheter no longer conforms to the curvature of the anatomy. This change of the geometry of the system within the anatomy can lead to inaccurate stent positioning.

Delivery systems which utilize the "pull-back" type technique usually require removal of "slack" developed between the outer sheath and the inner catheter member upon which the stent is mounted. Generally, the exposed catheter, i.e. the portion of the outer member which remains outside of the patient, must usually be kept straight or relatively straight during deployment. Failure to do so may result in deploying the stent beyond the target area and can cause the stent to bunch up. This phenomenon occurs because the inner catheter member tends to move forward when the outer sheath is retracted. The reason why this happens is because the inner catheter member and outer catheter member are typically the same length prior to stent deployment. The length of the exposed catheter, again, the portion of the outer catheter which extends between the deployment handle and the insertion point in the patient, however, is usually fixed. When the outer sheath is retracted proximally into the deployment handle during deployment, the length of the exposed outer sheath tends to shorten. The inner catheter member, however, remains the same length as it is held fixed in the deployment handle. However, the outer sheath tends to shorten during deployment, thus changing the shape of the exposed portion of the catheter. This shape change occurs because the outer sheath wants to straighten out once it's being retracted. Since the inner catheter member is fixed proximally within the deployment handle, it will move distally as the outer sheath is retracted. As a result, the movement of the inner catheter member caused by the retraction of the outer sheath can cause the stent to deploy prematurely and at a location beyond the targeted site. As a result, less than accurate deployment of the stent can occur.

This problem usually does not exist when the delivery system is kept straight during deployment as the outer sheath is allowed to slide proximally relative to the inner catheter member. However, if the delivery system is not kept straight during deployment, then the inner catheter member has this tendency to move distally during deployment. This change in the shape of the exposed catheter forces the inner catheter member to change shape as well in order for the inner catheter member to maintain the same length as the outer sheath. Since the inner catheter member is fixed within the deployment handle, it can only move distally. Consequently, the inner catheter member moves distally along with the mounted stent, causing the stent to be deployed beyond the targeted site in the patient's anatomy.

The above-described stent delivery systems also can be somewhat difficult to operate with just one hand, unless a mechanical advantage system (such as a gear mechanism) is utilized. Often, deployment with one hand is desirable since it allows the physician to use his/her other hand to support a guiding catheter which may be utilized during the procedure. The above-described stent delivery systems should not be susceptible to any axial movement of the catheters during stent deployment. Even a slight axial movement of the catheter assembly during deployment can cause some inaccurate placement of the stent in the body lumen. Some stent delivery systems employ a control handle which utilizes a pistol grip actuator that requires the physician to repeatedly pull back a trigger mechanism to cause the outer sheath to retract. In doing so, the physician usually creates a backwards force on the delivery system which also can cause the catheter portion of the delivery system to move within the patient's vasculature, resulting in less than accurate placement of the stent within the patient. Also, some of these stent delivery systems have a limited range of retraction of the outer sheath which can limit the use of the delivery system to smaller medical devices which require only a small amount of retraction in order to expand the device. Larger medical devices, such as vasculature grafts, cannot be deployed because the control handle of the system cannot retract the outer sheath a sufficient length in order to expose the entire graft.

Thus, there is a need for a delivery system for delivering and deploying a self-expanding medical device, such a stent, which prevents the axial movement of the inner catheter member relative to the outer sheath to prevent the inner catheter member from moving forward during deployment. Such a delivery system also should also compensate for any slack that may be present in the delivery system and should prevent the inner catheter member from moving forward within the patient's vasculature as the outer restraining sheath is being retracted from the self-expanding medical device. Such a delivery system would be beneficial if it allowed the physician to actuate the system with only one hand, thus allowing the physician to use his/her other hand during the procedure. The present invention disclosed herein satisfies these and other needs.

SUMMARY OF THE INVENTION

The present invention is directed to a delivery system for delivering and more accurately deploying a medical device, such as a stent, to the target site in a body lumen. The delivery system in accordance with the present invention incorporates unique features which facilitates minimal movement during device deployment, accurate placement, and single-handed system operation. While the delivery system can be used to deploy any self-expanding stent, it also can be used to deploy other self-expanding medical devices, including medical devices which are not self-expanding as well.

In one aspect of the present invention, the delivery system include a control handle and a catheter portion which is designed for advancement to a target area in a patient's body lumen over a deployed guide wire using "over the wire" techniques known in the art. The catheter portion includes an inner catheter member having a proximal portion attached within the control handle and a distal portion upon which the medical device is mounted in a collapsed position. An outer restraining member extends over the inner catheter member in a coaxial arrangement. The outer restraining member holds the medical device in the collapsed position until the device is to be deployed. If the medical device is not self-expanding, the outer restraining member does not necessarily restrain the device, but provides a protective cover for the device. The outer restraining member is retractable to release the medical device by a retraction mechanism housed in the control handle. The control handle includes a rotatable thumbwheel which is easily moveable to provide a manual mechanism for retracting the restraining sheath. The control handle immobilizes the inner catheter member, preventing it from moving relative to the outer restraining member during deployment. The control handle allows the delivery system to be operated by just one hand, freeing the physician's other hand for other purposes, such as stabilizing the guiding catheter during deployment of the medical device.

In one aspect of the present invention, the catheter portion includes an outer sheath which is utilized to stiffen the catheter portion of the delivery system on that the inner catheter member will not change shape outside the body when the outer restraining member is retracted to deploy the medical device. The outer sheath extends at least partially over the length of the outer restraining member in a coaxial relationship in order to create a conduit between the control handle and the point of insertion into the patient. This outer sheath helps to reduce frictional forces which may be created with the medical device that is inserted into the patient to obtain entry for the catheter portion, such as a rotating hemostatic valve (RHV), or other similar device, and helps to prevent the inner catheter member from moving distally as the outer restraining sheath is being retracted via the control handle.

In another aspect of the present invention, the outer sheath is attached to a strain relief member which is threadingly engaged with the control handle. In this particular aspect of the invention, the proximal end of the strain relief has a channel formed in it which is designed to receive a tab-like projection formed in a recess of the control housing in order to allow the strain relief member to be threaded onto the control handle. Depending upon physician preference, the outer sheath can either remain or be removed from the control handle during use.

In another aspect of the present invention, the retraction mechanism of the control handle allows the outer restraining member to be retracted in a proximal direction only and includes a stop mechanism which prevents the retraction mechanism from prematurely deploying. The control handle allows the physician to actuate the retraction mechanism using a simple thumb motion on the thumbwheel which helps to prevent unwanted forces from acting on the control handle which can typically be developed when a pistol-like actuated control handle is utilized. As a result, a more accurate placement of the medical device may be achieved.

The inner catheter member has a guide wire lumen which extends from the distal end of the inner catheter member to the proximal end to allow a guide wire to be used to advance the catheter portion to the target area in the body lumen in an "over the wire" technique. In this regard, the catheter/medical device can be introduced within the patient's vasculature in a conventional Seldinger technique through a guiding catheter. The distal end of the inner catheter member includes a soft, low profile tip assembly with a radiopaque marker.

These and other advantages of the present invention become apparent from the following detailed description and the accompanying exemplary drawings.

BRIEF DESCRIPTION OF THE DRAWINGS

FIG. 4 is a cross sectional view of the control handle of FIG. 1.

FIG. 5 is an enlarged cross-sectional view of the retraction mechanism of the control handle of FIG. 4.

FIG. 6 is a cross-sectional view of the control handle of FIG. 4 in which the rack and pinion portion of the control handle has been partially retracted.

FIG. 7 is a perspective view showing the proximal end of the strain relief portion of the catheter system which is attached to the outer sheath utilized in conjunction with the present delivery system.

DETAILED DESCRIPTION OF THE PREFERRED EMBODIMENTS

The present invention relates to a delivery system for delivering and deploying a medical device into a target site in a patient's body, such as a body lumen. For sake of illustration, the following exemplary embodiments are directed to a delivery system for delivering and deploying a self-expanding stent, although it is understood that the present invention is applicable to other medical devices which are implantable in a body lumen as well as other parts of the body. Additionally, the medical device can be either a self-expanding device or a non self-expanding device.

Figure 1:
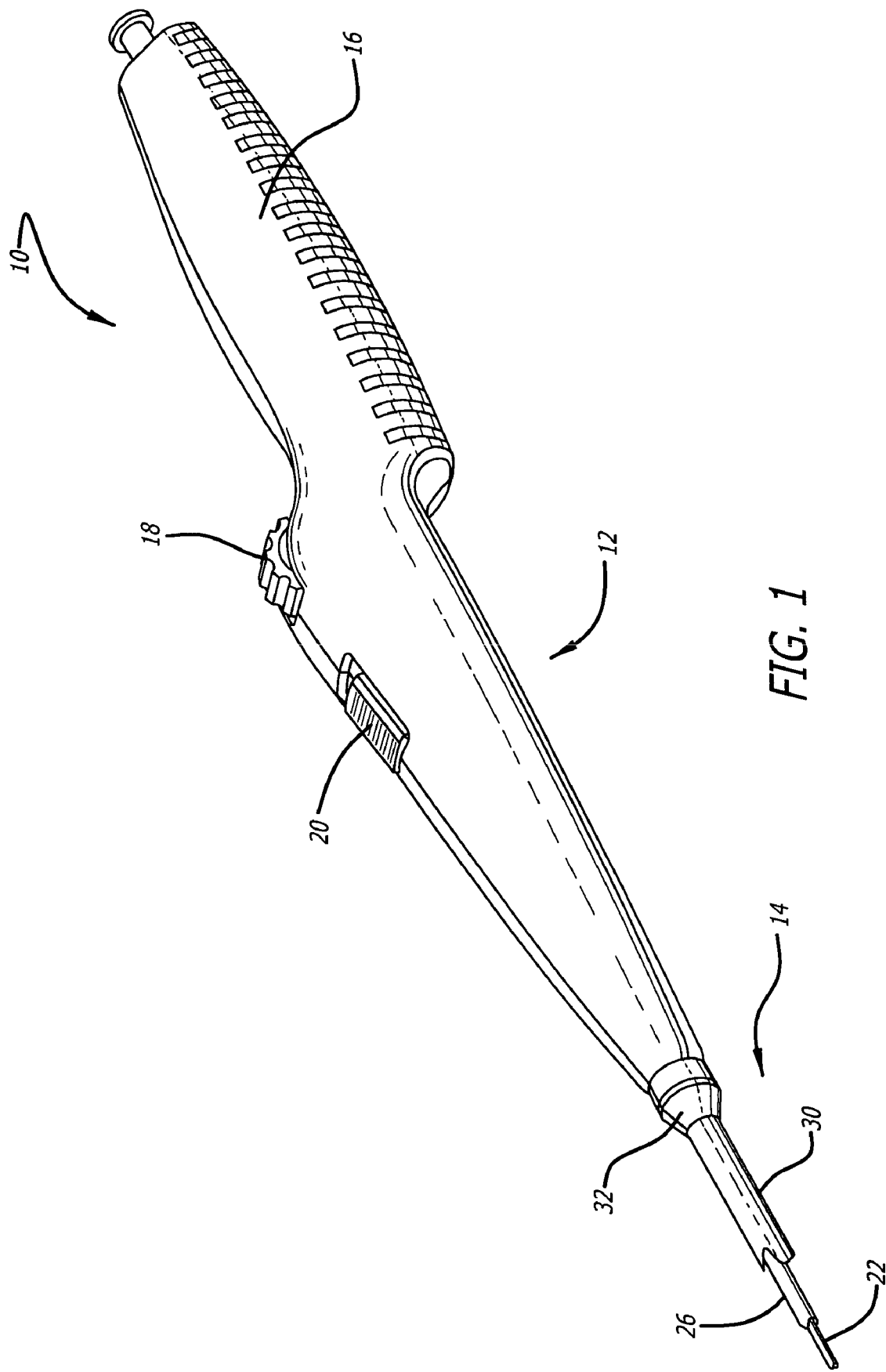
FIG. 1 is a perspective view showing a control handle which forms part of the delivery system of the present invention.
Figure 2:
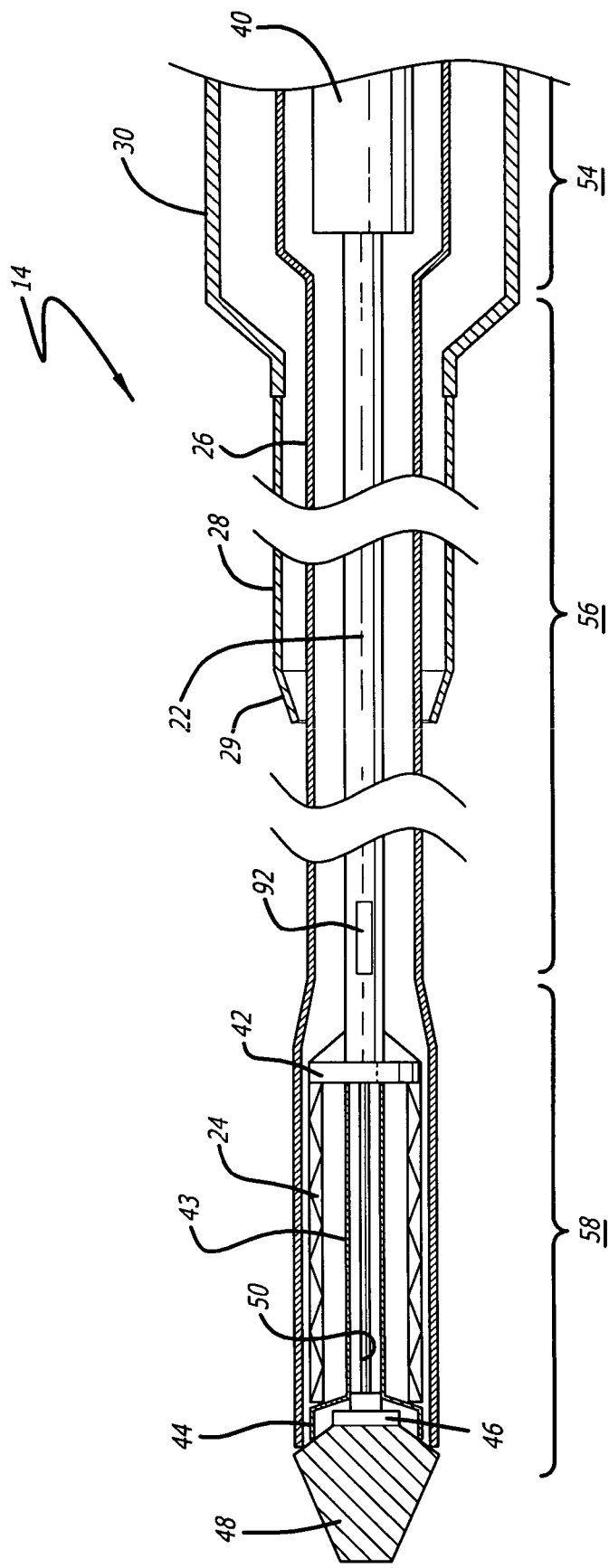
FIG. 2 is an elevational view, partially in section, showing a schematic representation of the catheter portion of the delivery system which attaches to the control handle.

Referring now to FIGS. 1 and 2, in one particular embodiment of the present invention, the delivery system 10 incorporating features of the present invention includes a control handle 12 and a catheter portion 14. As can best be seen in FIG. 1, the control handle includes a hand portion 16 which allows the physician to hold the control handle utilizing one hand. The control handle 12 also includes a rotatable thumbwheel 18 which allows the physician to retract the restraining sheath utilized to maintain the self-expanding medical device in its collapsed, delivery position near the distal end of the catheter portion 14 of the system. The hand portion 16 can be easily grasped by the physician and the thumbwheel 18 can be easily rotated by the physician to actuate the mechanism which pulls back the restraining sheath to expose the self-expanding stent to achieve deployment of the device within the patient. A lock mechanism 20 is utilized to maintain the catheter portion 14 of the device in a securely locked condition until the physician is ready to manipulate the thumbwheel 18 to deploy the medical device. The design of the control handle allows the physician to hold the hand portion 16 in either his/her right or left hand and easily manipulate the thumbwheel 18. Alternatively, the physician can grasp the portion of the control handle distal to the thumbwheel 18 if desired, and still be capable of easily rotating the thumbwheel 18 in order to retract the restraining sheath. This sleek design of the control handle allows added versatility when handling and deploying the delivery system made in accordance with the present invention.

Referring now specifically to FIG. 2, the catheter portion 14 is shown schematically as including an inner catheter member 22 which is adapted to carry the medical device, such as a self-expanding stent 24, near the distal end of the inner catheter member 22. An outer restraining member extends generally coaxially over the inner catheter member 22 and is designed to maintain the stent 24 in its collapsed delivery configuration until the stent is to be deployed by the physician. This outer restraining member 26 can be retracted via the control handle 12 in accordance with the present invention. A third catheter member forms the outermost catheter portion 14 of the system and is shown as an outer sheath 28 which is removably attached to the control handle 12. In this regard, the outer sheath 28 is coaxially disposed over the outer restraining member 26 and can be removably attached to the control handle 12 or attached to a strain relief 30 which is removably attached to a nose cone 32 forming part of the control handle 12. Further details on the construction of the removable strain relief 30 and its attachment to the nose cone 32 are described in greater detail below.

The outer sheath 28 is utilized in order to stiffen the catheter portion of the delivery system so that the arc of the inner catheter member 22 will not change shape outside the body when the outer restraining member 26 is pulled back to deploy the stent. In this regard, the inner catheter member 22 can be maintained in a stationary position relative to the control handle 12 so that the inner catheter member 22 will not move distally once retraction of the outer restraining member 26 commences.

Figure 3:
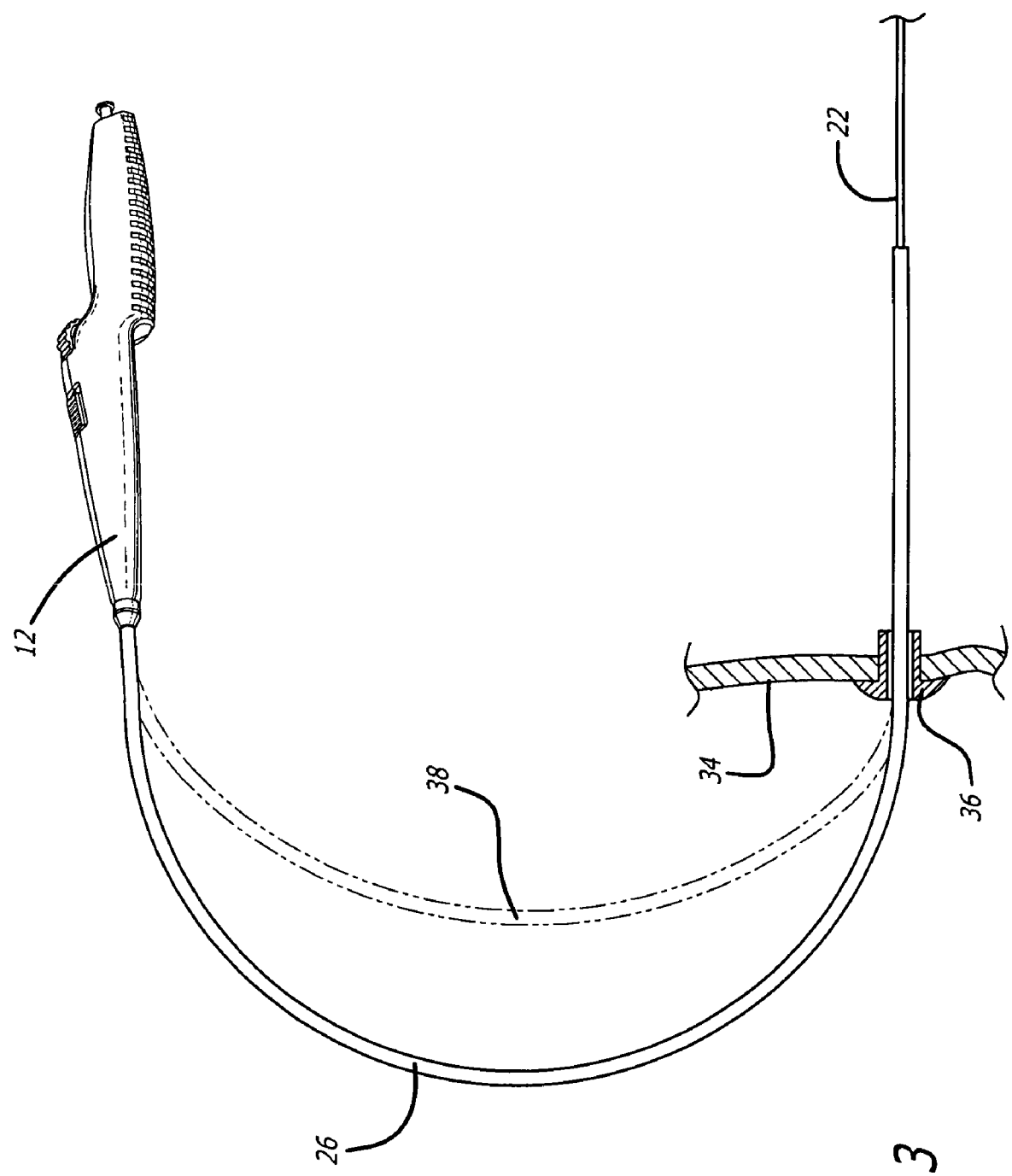
FIG. 3 is a perspective view of a delivery system showing the flattening of the arc during deployment in silhouette.

Referring specifically now to FIG. 3, the problem that exists when a delivery system does not utilize an outer sheath 28, such as the one made in accordance with the present invention, is described in greater detail. FIG. 3 shows the delivery system as it extends outside of the patient 34 (schematically represented in FIG. 3). A rotating hemostatic valve 36 is shown schematically inserted within the patient 34. In FIG. 3, the delivery system is shown without the outer sheath 28 connected to the control handle 12 and merely represents an outer restraining member 26 coaxially disposed over the inner catheter member 22. When the delivery system is maintained at a curvature with respect to the entry point, i.e. at the rotating hemostatic valve 36, the inner catheter member has a tendency to move distally during the retraction of the outer restraining member. FIG. 3 shows the presence of a curvature in the exposed portion of the catheter portion prior to deployment. In this state, the lengths of the inner and outer members are substantially the same. However, the outer restraining member tends to shorten during deployment, thus changing the shape of the exposed portion of the catheter. This shape change occurs because the outer restraining member wants to straighten out once it's being retracted. This change in the shape of the outer restraining member is shown in silhouette 38 in FIG. 3. Since the inner catheter member is fixed proximally within the control handle, it will move distally as the outer restraining member is retracted. As a result, the movement of the inner catheter member caused by the retraction of the outer restraining member can cause the stent to deploy prematurely and at a location beyond the targeted site. As a result, less than accurate deployment of the stent can occur.

The outer sheath 28 is designed to attach to the point of entry in the patient, for example the rotating hemostatic valve 36 located at the insertion opening in the patient's vasculature, to avoid the premature deployment of the stent since this outer sheath 28 creates a conduit that allows the outer restraining member 26 of the catheter portion 14 to move without excessive friction. The outer diameter of the outer sheath 28 can remain compatible to a specified sheath sizing or it can include a necked-down distal region 29 in which the inner and outer diameters of the outer sheath 28 is less than the remainder of the outer sheath. This necked-down region 29 helps to reduce the possibility of blood loss through the annular space formed between outer sheath and the outer restraining member. The outer sheath 28 ensures accurate deployment without the need to remove slack from the exposed catheter portion, i.e. the portion of the catheter which extends between the rotating hemostatic valve and the control handle. As a result, a physician utilizing the delivery system of the present invention may not be required to keep the exposed catheter portion straight or substantially straight in order to achieve accurate placement of the stent.

Referring again specifically to FIG. 2, the various components making up the catheter portion 14 of the delivery system 10 are described in greater detail herein. The inner catheter member 22 extends from the control handle 12 to a distal portion which includes a region for mounting the self-expanding stent 24. In one particular embodiment of the present invention, the inner catheter member 22 is a composite structure formed of two different type of tubing, each tubing having a specific function. FIG. 2 shows the inner catheter member 22 including a proximal portion 40, made from a hypotube, which extends within the control handle 12 as is shown in FIGS. 4-6. The distal portion 41 of the inner catheter member which is attached distal to the proximal portion 40 and can be made from polymide material which is braided with stainless steel which serves to provide a strong, but flexible, catheter portion in order to provide good trackability and pushability over a guide wire (not shown). The application of tensile force to the shaft of the outer restraining member 26 and outer sheath 28 during stent deployment can create an equal and opposite compressive force on the inner catheter member 22. For the outer restraining member 26 to retract (via the movement of the control handle 12) without causing the rest of the catheter portion 14 to buckle, the inner catheter member 22 must possess sufficient column strength to prevent buckling or deformation. Otherwise, buckling or deformation to the inner catheter member 22 can cause the distal end of the catheter portion 14 to move within the artery, causing inaccurate deployment of the stent. Therefore, the tubing used to form the distal portion 41 of the inner catheter member 22 should be fabricated from a tubular element which possesses sufficient rigidity to prevent unwanted buckling or deformation, yet is flexible enough to track along the torturous anatomy to the target site.

Alternative tubing includes a more flexible material such as polyethereketone (PEEK) or similar material which possess excellent compressive strength, yet is reasonably flexible. The proximal portion 40 can be made from hypotube which provides maximum strength, but is fairly rigid. However, this is not a concern since this proximal portion 40 of the inner catheter member 22 remains relatively straight within the control handle 12. The distal portion of the inner catheter member 22 must exit the guiding catheter and track through the torturous anatomy to reach the target site. Therefore, this portion must possess sufficient compressive strength, yet be fairly flexible.

As mentioned above, the inner catheter member 22 further includes the distal portion which has the stent 24 mounted thereto. The distal end of the inner catheter member 22 includes a stent holder 43 which is formed between a proximal abutting shoulder 42 and a distal abutting shoulder 44. These shoulders create an area for mounting the self-expanding stent 24 in its collapsed position. These shoulders 42 and 44 also help to maintain the stent on the stent holder of the inner catheter member 22 as the outer restraining member 26 is retracted. The proximal shoulder 42 provides an abutting surface which contacts the end of the stent in the event frictional forces act on the stent as the outer restraining member 26 is being retracted. A distal marker 46 made from a highly radiopaque material, such as tantalum or a platinum iridium alloy (Pt/IR 90%/10%), provides a visual reference point for the physician when utilizing fluoroscope or other imaging equipment. The shoulder 42 also can be made from a highly radiopaque material to serve as a visual marker as well. A soft tip 48 is attached to the inner catheter member 22 in order to create an atraumatic tip to help prevent snow plowing of the catheter portion as it is being delivered in an over-the-wire fashion along a guide wire. For example, the soft tip 48 can be made from a polymeric material such as polyether-block co-polyamide polymer sold under the trademark PEBAX 25b-barium sulfate, a soft material which includes a radiopaque element that provides an additional visualization point for the physician during fluoroscopy.

A guide wire lumen 50 extends along the entire length of the inner catheter member 22 and can be made from a tri-layer of materials such as PEBAX 72D, primacore and HDPE. The guide wire lumen 50 extends through the soft tip 48 and is attached to a luer fitting 52 mounted within a recess formed in the control handle 12. The luer fitting 52 permits the control handle to be attached to syringes used to flush the system and also provides an opening for the guide wire. The luer fitting 52 is attached at the proximal end of the hypotube and fits within the recess formed in the control handle to prevent the inner catheter member 22 from moving relative to the outer restraining member 26 during stent deployment. The luer fitting 52 can be attached to the hypotube 40 by gluing the fitting and hypotube together using a suitable adhesive. It should be appreciated that the mounting of the inner catheter member 22 to the control handle 12 can be achieved in any number of ways without departing from the spirit and scope of the present invention.

This guide wire lumen 50 can be made from other materials which provide a low friction interface between the delivery catheter and the guide wire which is used in the procedure to advance the catheter portion to the target site using over-the-wire techniques that are well known in the art. For example, the guide wire lumen can be made from tubing which is compatible with a 0.014 inch guide wire for an over-the-wire configuration.

The guide wire lumen 50 extends from the distal end of the inner catheter member 22 to the proximal end to allow a guide wire to be used to advance the catheter portion 14 (with mounted stent 24) to the target area in the body lumen in an "over the wire" technique. In this regard, the catheter portion 14 can be introduced within the patient's vasculature using, for example, a conventional Seldinger technique through a guiding catheter.

The outer surface of the inner catheter member can be coated with a silicone lubricant such as Microgilde manufactured by Advanced Cardiovascular Systems, Inc., Santa Clara, Calif., to further reduce the amount of frictional buildup between the outer restraining member and inner catheter member.

In one embodiment of the present invention, the outer restraining member 26 is a composite structure formed from three different sized tubing materials, each tubing material having a specific function. The outer restraining member 26 is shown including a proximal portion 54 which extends within the control handle 12 and is attached to the mechanism which produces the retraction force needed to retract the outer restraining member from the stent. This proximal portion 54 of the outer restraining member 26 is designed to move axially (along the longitudinal axis of the control handle). This proximal portion 54 of the outer member can be made from a material such as a polymide. The outer restraining member 26 also includes a mid-portion 56 which can also be made from a material such as a polymide or other similar material which provide a low profile, yet is strong enough to develop the pushability needed as the delivery system is moved along the guide wire in an over-the-wire delivery. This mid-portion 56 can be made with tubing having a different wall thickness than the proximal portion 54. The outer restraining member 26 also includes a distal portion 58 which has a larger inner diameter than the tubing forming the mid-portion 56 in order to obtain the necessary diameter to maintain the collapsed self-expanding stent 24 in position on the system. This portion of the outer restraining member 26 is designed to hold the stent 24 in its compressed or collapsed state and is retracted by actuating the thumbwheel 18 of the control handle 12 which proximally moves the restraining member while maintaining the inner catheter member 22 stationary during stent deployment. The distal portion 58 can be made from a material such as polymide or other suitable materials which will provide the necessary restraining force needed to keep the self-expanding stent in place. Since it is usually desired to have a low profile at this distal location of the catheter, a tubing having a thinner wall thickness can be utilized.

Alternative material for forming the outer restraining member 26 includes material such as cross-linked HDPE. Alternative materials for the distal portion 58 include materials such as polyolefin which can be bonded to the mid-portion 56 of the outer restraining member 26. A material such as polyolefin is used since it has sufficient strength to hold the compressed stent and has relatively low frictional characteristics to minimize any friction between the stent and the tubing. Friction can be further reduced by applying a coat of silicone lubricant, such as Microgilde, to the inside surface of the distal portion 58 before the stent is loaded onto the stent holder.

The outer sheath 28 extends along a portion of the length of the outer restraining member 26 as is necessary to create the conduit for the length of the catheter which remains outside the patient. The length of this outer sheath 28 can be varied depending upon the size of the medical device mounted on the distal end of the inner catheter member 22. In this regard, the length of the outer sheath 28 generally can be as long as, or longer than, the guide catheter (not shown) utilized when the delivery system is placed in the patient's vasculature.

In one aspect of the invention, the outer sheath 28 includes the neck-down region 29 in which the inner diameter of the outer sheath 28 is comparable to the outer diameter of the mid-portion 56 of the outer restraining member 26. In this fashion, a fairly tight fit extends between these two catheter portions in order to minimize blood loss between these catheter portions. Since the distal portion 58 has a larger diameter than the tubing forming the mid-portion 56, the distal end of the outer sheath 28 should generally terminate a sufficient distance to allow the outer restraining member 26 to be fully retracted by the control handle 12, while preventing the larger diameter distal portion 58 from abutting the distal end of the outer sheath 28. In this regard, for example, if a 40 mm stent is mounted on the inner catheter member 22, then the length of the retraction needed to properly release the device would require that the distal end of the outer sheath 28 be at least 40 mm away from the transition portion where the mid-portion 56 translates to the distal portion 58 to allow the outer restraining member 26 to retract properly. If a longer length medical device is mounted on the inner catheter member 22 then the overall length of the outer sheath 28, of course, should be adjusted. It is also possible for the inner diameter of the outer sheath 28 to be at least as large as the outer diameter of the distal portion 58 of the outer restraining sheath 26 to allow proper retraction of the outer restraining sheath 26.

The outer sheath 28 can be made from materials such as polymide and other suitable materials. Other materials include polyetheretherketone (PEEK) and polyether-block co-polyamide polymer sold under the trademark purple PEBAX SA2032476. The strain relief 30 which is attached to the proximal end of the outer sheath can be made from a material such as Pebex 70D. As will be described in greater detail below, the strain relief 30 includes a proximal end 60 which can be threaded into the nose cone 32 of the control handle 12 to allow the physician to remove the outer sheath 28, if not needed.

Referring now to FIG. 7, the proximal end 60 of the strain relief 30 is shown in greater detail. As can be seen from this figure, the proximal end 60 includes a continuous channel 62 which creates a maze-like thread that allows the strain relief 30 to be removably attached to the control handle 12. This maze-like channel threads into the nose cone 32 and allows the outer sheath 28 to be connected or detached based upon physician preference. Referring specifically now to FIGS. 4 and 6, the channel 62 of the proximal end 60 is adapted to be threaded along a tab-like projection 64 which extends into the recess of nose cone 32 of the control handle 12. This tab-like projection 64 can be sized or shaped to fit within the channel 62. A projection stop element 66, which extends within this channel 62, acts like a detent once the proximal end 60 of the strain relief 32 has been threaded into the nose cone. This projecting stop 66 prevents the strain relief from being moved from the nose cone until the physician desires to remove the outer sheath from the control handle. In this manner, the area 68 adjacent to the projecting stop 66 is designed to contain the tab-like projection 64 until the physician is ready to remove the outer sheath. The physician can remove the outer sheath 28 by simply twisting the strain relief 32 to allow the tab-like projection 64 to move past the projecting stop element 66 and then be moved along the channel 62 until the projection 64 disengages from the channel. It should be appreciated that other coupling means could be formed or attached to the control handle, besides a tab-like projection 64, to receive the channel 62. Additionally, the outer sheath 28 does not have to be attached to the strain relief 30, but can be removably attached to the control handle itself. In this regard, the proximal end of the outer sheath can have a similar channel formed therein as is shown in FIG. 7.

The control handle 12 of the present delivery system 10 will be described in greater detail herein. Referring now specifically to FIGS. 4-6, a cross sectional view of the actuating mechanism housed within the control handle 12 is shown. The thumbwheel 18 of the control handle 12 is connected to the actuating mechanism which is adapted to retract the outer restraining member 26 relative to the inner catheter member 22 to allow the distal portion 58 of the outer restraining member to retract from the stent and cause it to self-expand into the target area. The actuator mechanism includes a slideable gear rack 70 which is disposed within a channel 72 formed along the length of the control handle 12. The slideable gear rack 70 is in turn attached to a spur gear 74 which engages the gears 76 on the gear rack 70. The thumbwheel 18 is connected directly to an actuating gear 78 which rotates as the thumbwheel is rotated by the physician. In this regard, once the thumbwheel 18 is rotated, the spur gear 74 is rotated by the actuating gear 78 causing the gear rack 70 to move proximally within the channel 72 formed in the control handle. FIG. 6 depicts the gear rack 70 in a position in which the gear rack 70 has been somewhat retracted through the rotation of the thumbwheel 18. Since the delivery system 10 can be used with just one hand, the physician's other hand is free to perform other tasks, such as stabilizing the guiding catheter used during the procedure. By stabilizing the guiding catheter as well, enhanced accuracy in deploying the stent can be obtained A lock mechanism 20, as shown in FIGS. 4 and 5, extends into the control handle to prevent the gear rack 70 from moving until the physician is ready to deploy the stent. In this regard, the lock mechanism 20 includes a locking arm 80 which is designed to abut against a stop element 82 formed or attached to the gear rack 70. As can be seen in FIG. 5, the locking arm 80 is shown in an abutting relationship with the stop element 82 to prevent the gear rack 70 from moving proximally in order to prevent retraction of the outer restraining member 26. The lock mechanism 20 includes a cam-like spring 84 designed to slide along a surface 86 formed into the body of the control handle 12. When the lock mechanism 20 is moved proximally by the physician, the locking arm 80 moves upward and away from the stop element 82 to permit the stop element 82 to move past it. It should be appreciated that this is just one mechanism which can be utilized to prevent unwanted retraction of the outer restraining member 26.

A spring 88 is mounted on a tab or protrusion 90 formed on the body of the control handle 12. This spring 88 is designed to contact the distal surface 91 of the gears 76 forming the gear rack 70 to prevent the gear rack 70 from moving distally at any time. As a result the control handle 12 of the present invention is capable of moving the outer restraining member in one direction, namely proximally. In this regard, the spring 88 allows the control handle to store energy and prevents the physician from losing energy during deployment. The spring 88 accomplishes this by creating an abutting edge 89 which contacts the distal surface 91 of the gears 76, as is shown in FIG. 5, preventing the gears 76 from moving distally, but allowing movement of the gear rack 70 in a proximal direction. The spring 88 could alternatively be placed in an abutting arrangement with one of the gears of the other moveable components forming the retraction mechanism. For example, the spring 88 could be placed near and in contact with the spur gear or actuating gear in order to allow rotation in only one direction. It should be appreciated to those skilled in the art that still other ways of restricting movement of the gear rack and outer restraining member could be implemented without departing from the spirit and the scope of the present invention.

The delivery system of the present invention also includes a flushing system used to evacuate air from the system. It is important to evacuate air from the system when the delivery system is being used in a patient's vasculature since air bubbles can sometimes cause damage to vital organs. In other instances, it may be desirable to have a fluid pre-placed into the system to prevent the possible accumulation of blood between the outer restraining member and the inner catheter member since stagnated blood has the tendency to coagulate and cause thrombosis. An alternative flushing fluid besides saline could be an anti-clotting agent which can be placed in the annular space formed between the outer restraining member and the inner catheter member to minimize blood clotting. Such an anti-clotting agent includes heparin, which not only provides an anti-clotting factor, but also includes smooth deployment and reduces deployment forces. Additionally, if blood clots in the annular space, it would lead to higher deployment forces, non-deployments, and potentially partial deployments. An anti-clotting agent, such as heparin, also can be placed in the annular space formed between the outer sheath and the outer restraining member to prevent clotting of blood within this space as well. It should be appreciated other anti-clotting agents besides heparin could be utilized in the same fashion. For these reasons, it may be beneficial to pre-flush the system before placing the delivery catheter in the patient.

Referring now to FIG. 2, the flushing system consists of an opening 92 or several openings extending through the inner catheter member 22 in the area of where the distal portion 58 meets the mid-portion 56 of the outer restraining member 26. The openings are drilled through to the guide wire lumen 50 to effectively open up a passageway from the guide wire lumen to the annular space formed between the inner catheter member 22 and the outer restraining member 26. A syringe can be attached to the luer fitting 52 on the catheter handle 12 and sterile fluid can be pumped into the guide wire lumen 50 in order to flush air from the system. A mandrel (not shown) can be placed in the guide wire lumen at the tip 48 to block the flow of the sterile fluid through the distal tip. The sterile fluid is thus forced to flow out of the small openings 92 into the annular space formed between the inner catheter member and outer restraining member. The fluid eventually flows past the collapsed stent where the fluid and any air in the system will escape through the distal opening of the outer restraining member 26. Once fluid is observed dripping from the distal end of the outer restraining member 26, the mandrel can be removed since air has been evacuated from the system. Since the gap sizes are so small between the various components, capillary force prevents air from infiltrating the delivery system once the evacuation has been completed.

The components of the control handle can be made from conventional materials well-known in the medical manufacturing art. For example, the control handle can be made from a plastic or plastic-like material such as ABS plastic, as can the various other components including the locking mechanism, gears and gear rack.

It is to be understood that even though numerous characteristics and advantages of the present invention have been set forth in specific description, together with details of the structure and function of the invention, the disclosure is illustrative only and changes may be made in detail, such as size, shape and arrangement of the various components of the present invention, without departing from the spirit and scope of the present invention. It would be appreciated to those skilled in the art that further modifications or improvement may additionally be made to the delivery system disclosed herein without departing from the scope of the invention. Accordingly, it is not intended that the invention be limited, except as by the appended claims.

What is claimed is:

1. A system for delivering and deploying a medical device within a patient, the system comprising:
   a delivery catheter including an inner catheter member having a region for mounting the medical device thereon and an outer restraining member co-axially disposed over inner catheter member and the medical device, the outer restraining member being adapted for axial movement with respect to said inner catheter member;
   a control handle having a rotatable thumbwheel connected to a retraction mechanism, the inner catheter member having a proximal end attached to the control handle and the outer restraining member having a proximal end attached to the retraction mechanism, wherein rotation of the thumbwheel causes linear movement of the retraction mechanism to proximally retract the outer restraining member to uncover the medical device while the inner catheter member remains stationary, wherein the retraction mechanism includes a gear rack which is slideable within a channel formed in the control handle and a spur gear which directly engages the gears of the gear rack, the thumbwheel having an actuating gear attached thereto which engages the spur gear to cause the gear rack to move linearly within the channel when the thumbwheel is rotated;

stop means for preventing unintentional movement proximal of the gear rack; and means for allowing motion of the gear rack in only one direction within the channel, wherein the means for allowing motion of the gear rack in only one direction is a spring having an edge which contacts the distal surface of the gears forming the gear rack to prevent distal movement of the gear rack.

2. The delivery system of claim 1, wherein the inner catheter member includes a guide wire lumen extending from the proximal end of the inner catheter member to the distal end of the inner catheter member.

3. The delivery system of claim 1, further including means for evacuating air from the delivery catheter.

4. The delivery system of claim 1, further including an anti-clotting agent placed between the outer restraining member and the inner catheter member.

5. The delivery system of claim 1, wherein the medical device is a self-expanding medical device.

6. The delivery system of claim 1, further including:
an outer sheath which extends co-axially over a portion of the outer restraining member.

7. The delivery system of claim 6, wherein the outer sheath is removably attached to the control handle.

8. The delivery system of claim 6, wherein the proximal end of the outer sheath is attached to a strain relief member which is removably attached to the control handle.

9. The delivery system of claim 8, wherein the strain relief member has a proximal end which includes a channel formed therein and the control handle has a distal recess formed therein and a tab-like member extending into the distal recess, the channel being adapted to receive the tab-like member to allow the strain relief member to be threadingly engaged with the control handle.

10. The delivery system of claim 9, further including a projection extending into the channel formed on the strain relief member which forms an abutting surface that prevents the tab-like member from moving past it until a rotational force is placed on the strain relief member.

11. The delivery system of claim 6, further including an anti-clotting agent placed between the outer restraining member and the outer sheath.

12. The delivery system of claim 6, wherein the outer sheath has distal portion which has a smaller inner diameter than the proximal portion of the sheath.

13. A system for delivering and deploying a medical device within a patient, the system comprising:
a delivery catheter including an inner catheter member having a region for mounting the medical device thereon and an outer restraining member co-axially disposed over inner catheter member and the medical device, the outer restraining member being adapted for axial movement with respect to said inner catheter member;

a control handle having a rotatable thumbwheel connected to a retraction mechanism, the inner catheter member having a proximal end attached to the control handle and the outer restraining member having a proximal end attached to the retraction mechanism, wherein rotation of the thumbwheel causes linear movement of the retraction mechanism to proximally retract the outer restraining member to uncover the medical device while the inner catheter member remains stationary, wherein the retraction mechanism includes a gear rack having a plurality of gear teeth and a spur gear which engages the gear teeth of the gear rack, the thumbwheel having an actuating gear attached thereto which engages the spur gear to cause the gear rack to move linearly within the channel when the thumbwheel is rotated; and a spring having an edge which contacts the distal surface of the gear teeth of the gear rack to prevent distal movement of the gear rack.

14. The delivery system of claim 13, further including:
an outer sheath which extends co-axially over a portion of the outer restraining member.

15. The delivery system of claim 14, wherein the outer sheath is removably attached to the control handle.

16. The delivery system of claim 14, wherein the proximal end of the outer sheath is attached to a strain relief member which is removably attached to the control handle.

17. The delivery system of claim 16, wherein the strain relief member has a proximal end which includes a channel formed therein and the control handle has a distal recess formed therein and a tab-like member extending into the distal recess, the channel being adapted to receive the tab-like member to allow the strain relief member to be threadingly engaged with the control handle.

18. The delivery system of claim 17, further including a projection extending into the channel formed on the strain relief member which forms an abutting surface that prevents the tab-like member from moving past it until a rotational force is placed on the strain relief member.

* * * * *